(12) United States Patent
O'Keeffe et al.

(10) Patent No.: US 8,676,044 B2
(45) Date of Patent: Mar. 18, 2014

(54) DYNAMIC SAUNA

(75) Inventors: James T. O'Keeffe, Mountain View, CA (US); Aaron Michael Zack, Overland Park, KS (US); Martin C. Ku, Kansas City, MO (US); Ian Richard Kuklenski, Kansas City, MO (US); Steven J. Murray, San Francisco, CA (US)

(73) Assignee: Sunlighten, Inc., Overland Park, KS (US)

( * ) Notice: Subject to any disclaimer, the term of this patent is extended or adjusted under 35 U.S.C. 154(b) by 440 days.

(21) Appl. No.: 12/426,762

(22) Filed: Apr. 20, 2009

(65) Prior Publication Data
US 2010/0017953 A1 Jan. 28, 2010

Related U.S. Application Data

(63) Continuation of application No. 12/205,597, filed on Sep. 5, 2008, now abandoned, which is a continuation-in-part of application No. 12/051,521, filed on Mar. 19, 2008.

(51) Int. Cl.
*A21B 2/00* (2006.01)

(52) U.S. Cl.
USPC .............................................. 392/416; 4/524

(58) Field of Classification Search
USPC ............... 392/407, 416; 4/527; 219/385, 480, 219/450.1, 492
See application file for complete search history.

(56) References Cited

U.S. PATENT DOCUMENTS

| | | | |
|---|---|---|---|
| 6,255,786 B1 * | 7/2001 | Yen ............................... | 315/291 |
| 6,489,614 B1 * | 12/2002 | Deguchi et al. ............. | 250/338.1 |
| 7,135,035 B1 * | 11/2006 | Dimmick ........................ | 607/90 |
| 2004/0188415 A1 | 9/2004 | Lee | |
| 2005/0256554 A1 * | 11/2005 | Malak ............................ | 607/88 |
| 2007/0033069 A1 | 2/2007 | Rao et al. | |
| 2007/0050903 A1 * | 3/2007 | Sappenfield et al. ............. | 4/524 |
| 2007/0110411 A1 * | 5/2007 | Bergstein ..................... | 392/379 |
| 2007/0206364 A1 * | 9/2007 | Swei et al. .................... | 361/748 |
| 2008/0036383 A1 * | 2/2008 | Lin .............................. | 313/634 |

FOREIGN PATENT DOCUMENTS

WO WO-2007117234 * 10/2007

OTHER PUBLICATIONS

Non Final Office Action of U.S. Appl. No. 12/051,521, mailed Nov. 8, 2011.
Final Office Action of U.S. Appl. No. 12/051,521, mailed Jul. 16, 2012, 22 pages.
Non Final Office Action in U.S. Appl. No. 12/051,521, mailed Feb. 6, 2013, 17 pages.

* cited by examiner

*Primary Examiner* — Henry Yuen
*Assistant Examiner* — Phuong Nguyen
(74) *Attorney, Agent, or Firm* — Shook Hardy & Bacon LLP

(57) ABSTRACT

Systems and methods are provided for controlling infrared radiation (IR) sources of a sauna including tuning IR wavelength-ranges and radiated power-levels of IR sources, and directing IR to locations on a user's body. In one illustrative embodiment, a sauna may be provided having adjustable heat sources to emit IR at any wavelength resulting in a desirable radiation treatment for the sauna user. In another illustrative embodiment, a method is provided for tuning IR sources in a sauna.

12 Claims, 12 Drawing Sheets

DYNAMIC SAUNA

CROSS-REFERENCE TO RELATED APPLICATIONS

This application is a continuation of patent application Ser. No. 12/205,597, entitled "DYNAMIC SAUNA" and filed on Sep. 5, 2008 which was a continuation-in-part of application Ser. No. 12/051,521, entitled "DYNAMIC SAUNA" and filed on Mar. 19, 2008.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter. The present invention is defined by the claims below but, summarily, embodiments of the present invention are directed toward methods and systems for independently controlling the temperature of heat sources such as heat sources in a sauna. More particularly, the present invention permits independent control of infrared radiation (IR) sources within a sauna, including tuning peak IR frequency emission ranges and radiated power levels of IR sources and targeting those sources at desired locations on a user's body. For example, various IR sources may be located within a sauna such that the IR sources are each pointed at a particular part(s) of a user's body in normal use, thereby permitting the selective warming of particular portions of a user's body.

Heating elements in accordance with the present invention permit a user to select one or more temperatures (or peak-infrared wavelength), with different temperatures/peak wavelengths being selectable for different heating elements. In accordance with the present invention, multiple heating elements (potentially emitting at different, selected peak wavelengths) may be combined into a single compact area. Further, IR heating elements in accordance with the present invention may generate and withstand temperatures associated with traditional saunas, at which air convection currents form. Accordingly, heating elements in accordance with the present invention may be used to produce both IR sauna experiences and traditional sauna experiences, whereas previously a given sauna heating element was either a traditional heating element (such as a hot rock or steam, for example) or an IR heating element.

A first aspect of the present invention relates to a sauna including a plurality of IR emitters operable to emit IR over specified wavelength-ranges, at least one driver module for operating the emitters, and a heat control module for facilitating control of the infrared emitters. For example, at least one IR emitter may comprise one or more arrays of light emitting diodes (LEDs) capable of emitting IR. An additional example may comprise one or more arrays of LEDs and one or more non-LED heating elements. A non-LED heating element may comprise, for example, a high resistance polyamide, a ceramic heater, a carbon black based heater, or any other type of infrared emitting element, some of which are described further herein. In this fashion, one or more peak IR wavelengths may be selected. Further, the absolute and/or relative power of one or more IR peaks may be selected. The wavelength and/or power of an IR peak may also be varied over time or distance by the driver. Such variance may be based upon user settings and/or selections or may be predetermined.

In a second aspect, a method is provided for using a sauna including receiving information related to wavelength-ranges of IR, conveying at least a portion of this information to one or more driver modules, and emitting IR from one or more emitters that are coupled to the one or more driver modules. The method further includes emitting IR having a wavelength-range that corresponds to the received information relating to one or more wavelength ranges of IR. In one illustrative embodiment, IR of a first wavelength-range is radiated from a first emitter and directed to a first location on a user's body, and IR of a second wavelength-range, different than the first wavelength range is radiated from a second emitter and directed to a second location on the user's body. Accordingly, a sauna user may select the wavelength of IR received during sauna use, and may even further select different IR wavelengths for different body portions and/or times.

In a third aspect a method is provided for tuning IR heating in a sauna. The method includes receiving information related to one or more IR wavelength-ranges; receiving corresponding information related to IR radiated output power-levels; and emitting, from one or more infrared sources, IR having wavelength-ranges and power-levels that correspond to the received information. In one embodiment, the information related to one or more IR wavelength-ranges and corresponding information related to IR radiated output power-levels may be provided by a user. In another embodiment, this information may be provided by a computing device.

In a fourth aspect of the present invention, infrared heaters with adjustable outputs are provided. For example, IR LEDs and non-LED IR sources such as a high resistance polyimide film, a ceramic heater, a carbon black based heater, or any other type of infrared emitting element, some of which are described further herein, may be used in various combinations. In this way, a desired peak IR wavelength(s) may be obtained for use in a variety of heating applications.

In a fifth aspect of the invention, an IR heater may have two or more portions designed to operate at different temperatures and produce multiple peak IR wavelengths. For example, a high resistance polyimide film may have two or more portions that operate at different temperatures, thereby outputting different peak IR wavelengths. In this example, the two or more portions of a high resistance polyimide film may be fixedly or adjustably set to operate at their respective temperatures.

In a sixth aspect of the present invention, the peak wavelength and power output of an infrared heater, can be independently controlled. Instead of controlling both output power and peak IR wavelength by varying current to a single heating element, the present invention provides independent control of different portions of an IR heater. By independently controlling a plurality of independent heater portions, output power and peak wavelength may be controlled.

BRIEF DESCRIPTION OF THE DRAWINGS

The present invention is described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Figure 1:
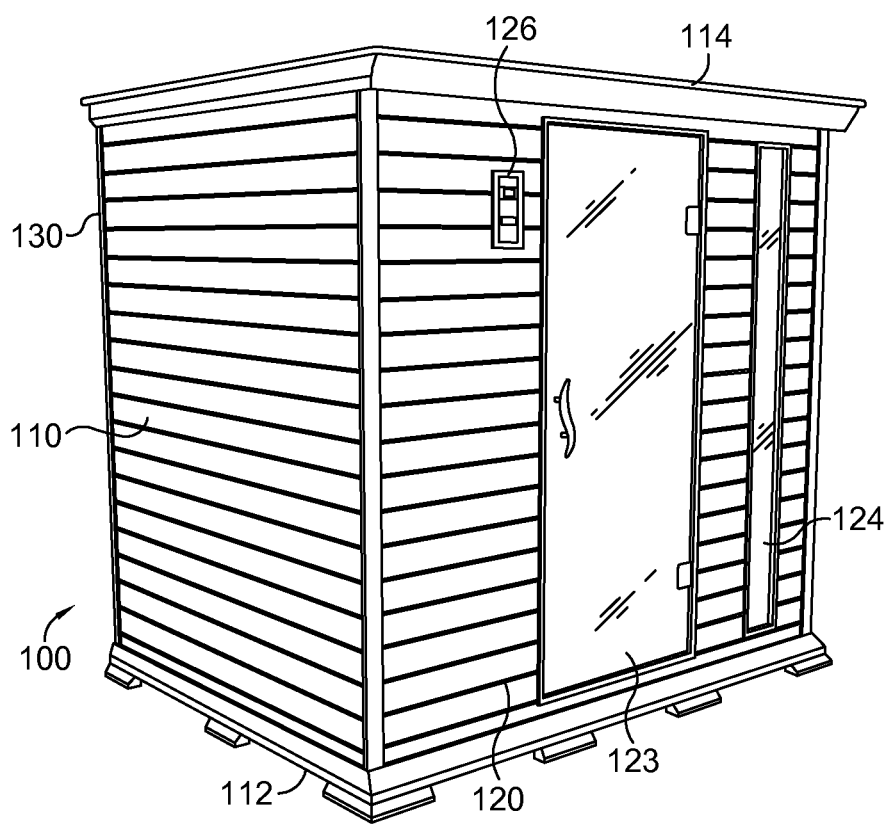
FIG. 1 is a perspective view of a sauna in accordance with an embodiment of the present invention.

Referring to FIG. 1, an exemplary sauna 100 is illustrated and generally includes a base panel 112, upright side panels 110 extending upwardly from base panel 112, a top panel 114 surmounting the side panels 110 so as to define a sauna enclosure. The sauna illustrated in FIG. 1 also includes a rear panel 130 and a front panel 120 having a door 123 disposed therein. It will be appreciated by those skilled in the art that the door 123 may be made of any number of various materials such as, for example, glass, wood, or particle board. The front panel 120 has a window 124 disposed between the door 123 and one of the side panels 110. It will be further appreciated by those skilled in the art that the panels and other components of a sauna 100 could be built using wood, metal, ceramics, or any other material available.

In the illustrated embodiment, an external control panel 126 is also shown. As will be further described below, various embodiments of the present invention may have an external control panel 126 for controlling various sauna features such as, for example, heating, lighting, or entertainment devices. In other embodiments, a sauna may not have an external control panel 126, but only an internal control panel, as discussed below. In further embodiments, a sauna may be provided with an external control panel that is not attached to the sauna, but rather is at a remote location such as, for example, a desk or control station in a health club. All of these arrangements, and all combinations thereof, are intended to be within the ambit of the saunas described herein.

Although the illustrated sauna has a generally rectangular configuration, it is entirely within the ambit of the present invention to provide other sauna configurations. For example, in one embodiment a sauna may be provided that has upright panels extending upwardly from the base panel at an angle so as to present a different polygonal shape. In another embodiment, a sauna may be configured so that it can fit comfortably in a corner of a room such as, for example, the Signature™ Corner sauna available from Sunlight Saunas, Inc. of Kansas City, Kans. In still a further embodiment, a sauna may be configured as a circular shaped modular sauna with interconnected panels. In one embodiment, a sauna may be provided that is configured with a semi-hemispherical shape for accommodating a single user such as, for example, the Solo System® available from Sunlight Saunas, Inc. of Kansas City, Kans.

Figure 2:
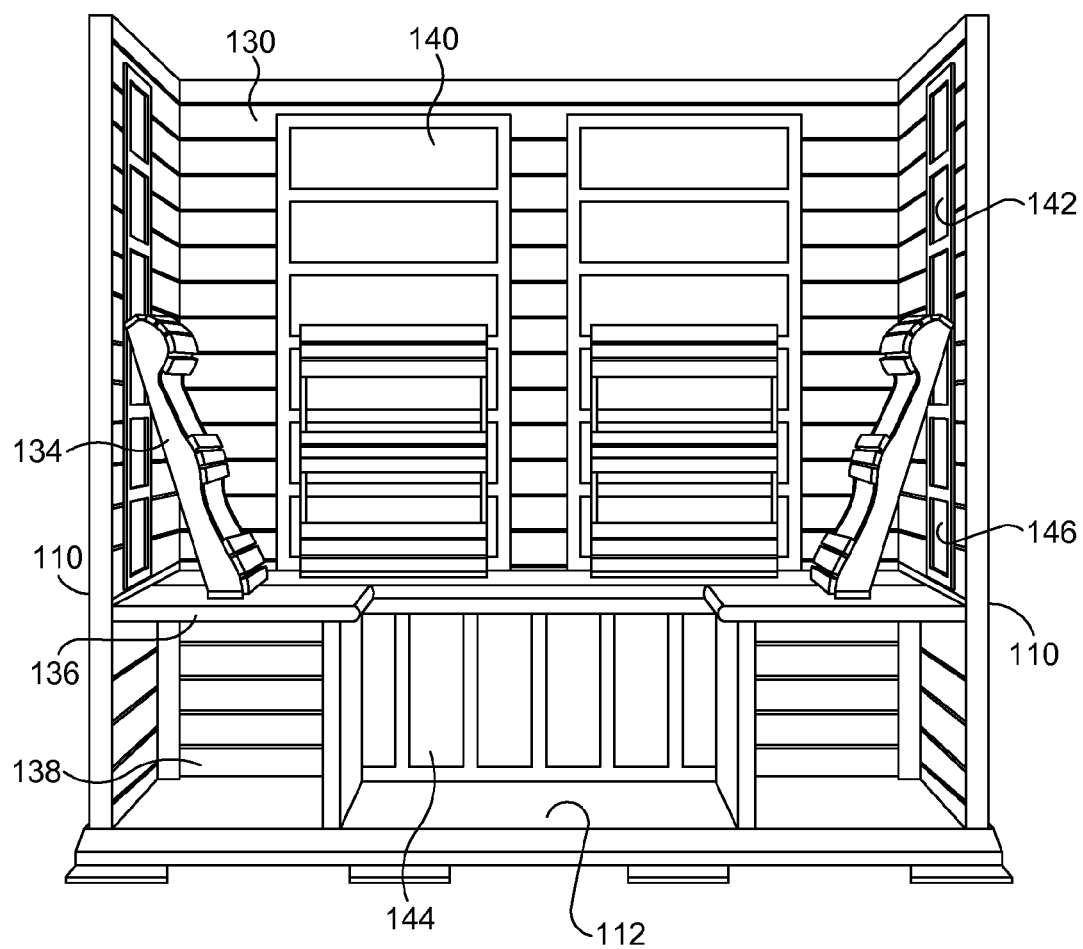
FIG. 2 is a cut-away front view of a sauna in accordance with an embodiment of the present invention.

Turning now to FIG. 2, a cut-away front view of a sauna such as the sauna 100 illustrated in FIG. 1 is shown. As illustrated, in one embodiment of the present invention, the sauna 100 may include one or more seating structures 136, such as benches, chairs, or other seating structures. The seating structures 136 may be disposed adjacent to any of the various internal walls of the sauna such as for example, the side walls 110 or the back wall 130. In various embodiments, such as the one depicted in FIG. 2, the sauna may include open spaces 138 disposed underneath the seating structures 136 and adjacent the interior walls 110 or 130. The open spaces 138 may be left open, used for storage, used to house other sauna feature devices, such as, for example, a computing device as described below, or may be used for any other purpose and in any other manner known in the art. In the illustrated embodiment, the sauna 100 is also provided with backrests 134 disposed on top of the seating structures 136 for supporting a user in an upright, seated position.

Additionally, the sauna 100 is equipped with heat sources 140,142,144,146, which are operable to heat the enclosure. The heat sources 140,142,144,146 are preferably configured to emit infrared radiation at varying wavelengths within the sauna so as to provide both heating and desirable IR treatment. In some embodiments, the heat sources may be adjustable to emit infrared radiation at any wavelength within the infrared wavelength spectrum such as, for example, near infrared, mid infrared, or far infrared. The heaters may include, for example, carbon-black-containing planar heating elements such as for example, Solocarbon® heat sources available from Sunlight Saunas, Inc. of Kansas City, Kans. The heaters may also comprise IR LEDs and/or other IR emitters as further described herein. Those ordinarily skilled in the art will appreciate that such heat sources 140,142,144, 146 provide a dry sauna with infrared treatment. As described further herein, IR emitters in accordance with the present invention may be used to create a "traditional" sauna experience, either by itself or in conjunction with a dry IR sauna experience. Additionally, certain wavelength settings may be adapted for particular treatment types such as, for example, detoxification, weight loss, pain management, and the like.

However, one of skill in the art will note that certain aspects of the present invention are not limited to such a sauna (e.g., certain principles apply to other types of saunas, such as steam saunas) or heaters (e.g., traditional coil heaters, etc.) or even at all. Similarly, although the exemplary embodiment illustrated in FIG. 2 shows a plurality of heat sources, it will be appreciated that other embodiments of the present invention may include saunas with a single heat source such as, for example, a single infrared heat source, a heated rock heat source, or a wire heat source.

With continued reference to FIG. 2, the heat sources 140, 142,144,146 may be configured such that individual heat sources 140,142,144,146 or combinations of heat sources 140,142,144,146 may be selected to output wavelengths of radiation that are different than wavelengths of radiation emitted by other heat sources 140,142,144,146. Such a configuration may be optimized to achieve a zone-heating effect, where one or more heat sources 140,142,144,146 is situated in a zone that corresponds to a particular region on a user's body, thus providing a mechanism for concentrating different levels of heat to different parts of the user's body. In an embodiment, one or more heat sources corresponding to one or more zones may be turned off such that no heat is emitted in those zones. It will be readily appreciated by those skilled in the art that such arrangements may be advantageous for various therapeutic reasons.

For example, in the embodiment illustrated in FIG. 2, some heat sources 144 may be positioned in a zone corresponding to a user's calf region (i.e., the lower part of the leg). Other heat sources 146 may be positioned in a zone corresponding to a user's lower-back region, and further heat sources 140, 142 may be positioned in zones corresponding to various other regions of a user's back. Thus, for example, if a user wishes to apply more heat to a sore calf muscle than to the rest of the user's body, the user may be able to select a higher output from heat source 144, while selecting a lower output for heat sources 140, 142, and 146. In various embodiments, fewer heat sources than those illustrated in FIG. 2 may be used, and in various other embodiments, more heat sources than those illustrated in FIG. 2 may be used. Additionally, heat sources may be configured in any number of ways to define zones that correspond to any number of regions of a user's body. As will be readily appreciated by those skilled in the art, any number of various combinations of settings and configurations for the heat sources are contemplated within this description.

Figure 8:
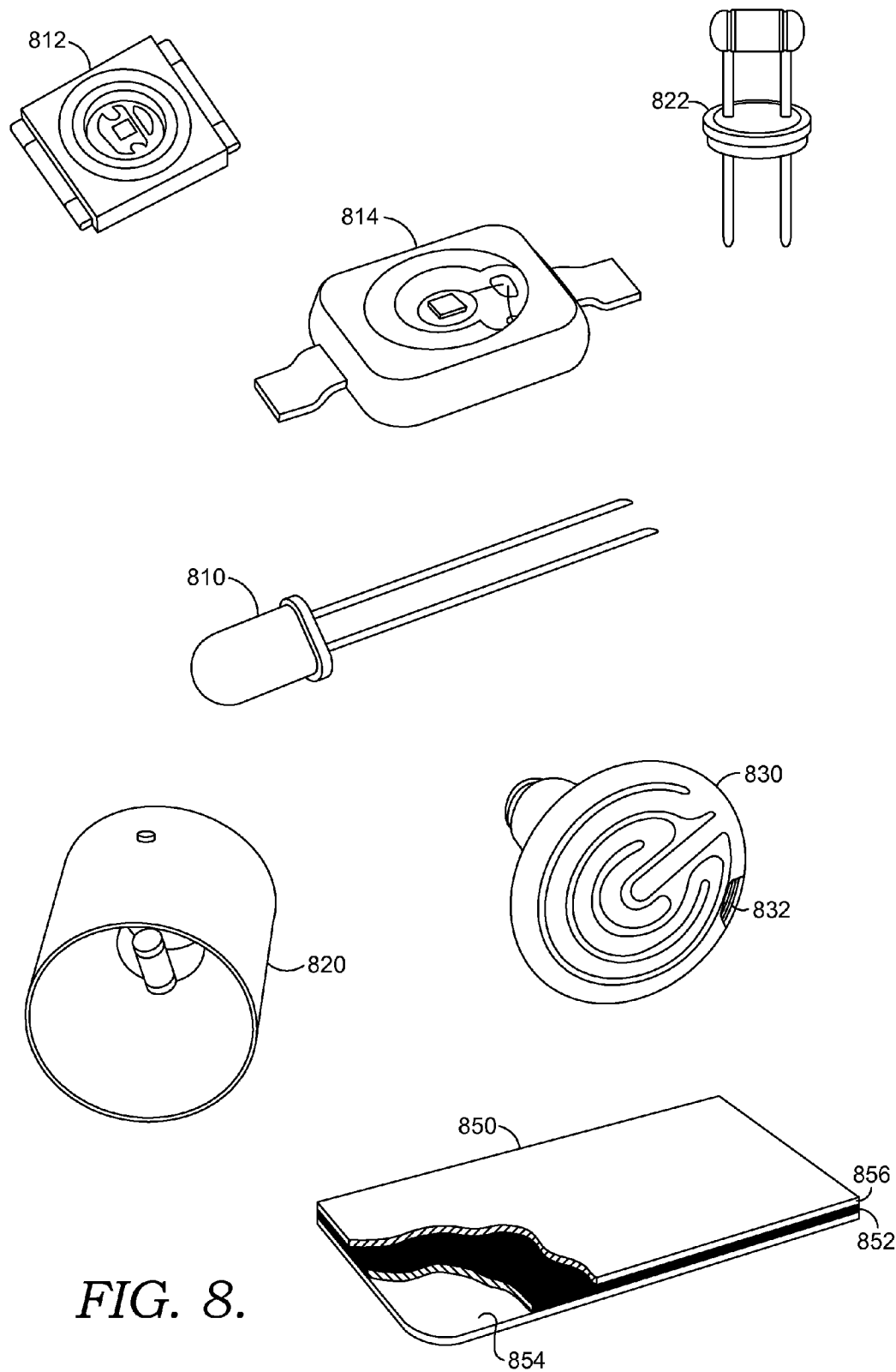
FIG. 8 is a view of various IR emitting elements that may be employed in the present invention.

FIG. 8 depicts examples of various IR emitting elements that may be employed in the present invention as component emitters of an IR heat source. Example IR emitters include infrared light-emitting diodes (LEDs) 810, 812, and 814; thermal IR emitting elements 820 and 822; ceramic-based IR emitting element 830, and planar heating element 850. Each element may provide IR at specific wavelengths and function as part of an IR emitter heat source. Any individual IR heat source may comprise one or more IR emitters, such as the examples illustrated in FIG. 8, and may further comprise multiple types of IR emitters that may possess different output properties.

Continuing with FIG. 8, LEDs 810, 812, and 814 may be surface-mountable such as LEDs 812 and 814. The semiconductor in the LEDs may be chosen to provide IR at specific wavelength ranges. For example, semiconductors using Gallium Arsenide (GaAs) or Gallium Aluminum Arsenide may be used to provide LEDs capable of emitting near-infrared radiation. Carbon-nanotubes may also be used, either in addition to or in place of other semiconductors. LEDs emitting mid- or far-infrared may also be used either alone or in combination with near-infrared LEDs or other elements, such as those described herein. The beam-angle of the LEDs may be chosen to facilitate targeting IR at specific locations. One example LED suitable for use in some embodiments of the present invention is the Everlight IR15-21C manufactured by Everlight Electronics Co. Thermal IR emitting elements 820 and 822 may comprise a coiled resistance wire, having high emissivity in the infrared spectral region, coiled over an aluminum substrate. One example thermal IR emitting element suitable for use in embodiments of the present invention is the IR-12K manufactured by Boston Electronics. Ceramic-based IR emitting element 830 may include an infrared ceramic heat bulb or ceramic heat emitter comprising wire 832 encapsulated in with alumina. One example ceramic-based IR emitting element suitable for use in embodiments of the present invention is the Ceramic Heat Wave Lamp manufactured by Exo Terra®, a subsidiary of Hagen, Inc. of Montreal, Canada. Planar heating element 850 may comprise a high-emissivity substrate 852 deposited on a surface 854 or alternatively between surfaces 854 and 856. Surfaces 854 and 856 may be made of heat-tolerant materials such as, for example, fiberglass, plastic, glass, ceramic, or any suitable materials. High-emissivity substrate 852 may comprise carbon-black containing materials such as, for example, carbon-infused paper or fabric, carbon ink deposited onto surface 854 or 856, or other suitable carbon-based materials. One example planar heating element suitable for use in embodiments of the present invention is the Solocarbon® heat source available from Sunlight Saunas, Inc. of Kansas City, Kans. Alternatively, high-emissivity substrate 852 may comprise nano-particalized ceramic that may be deposited onto surface 854 or between surfaces 854 and 856. One example suitable for use in embodiments of the present invention is the Insuladd® nano-particalized ceramic spray-on coating from Insuladd Co. of Merritt Island, Fla. In another example embodiment, the nano-particalized ceramic may be mixed with a carbon-containing ink and deposited onto surface 854 or between surfaces 854 and 856.

Figure 9:
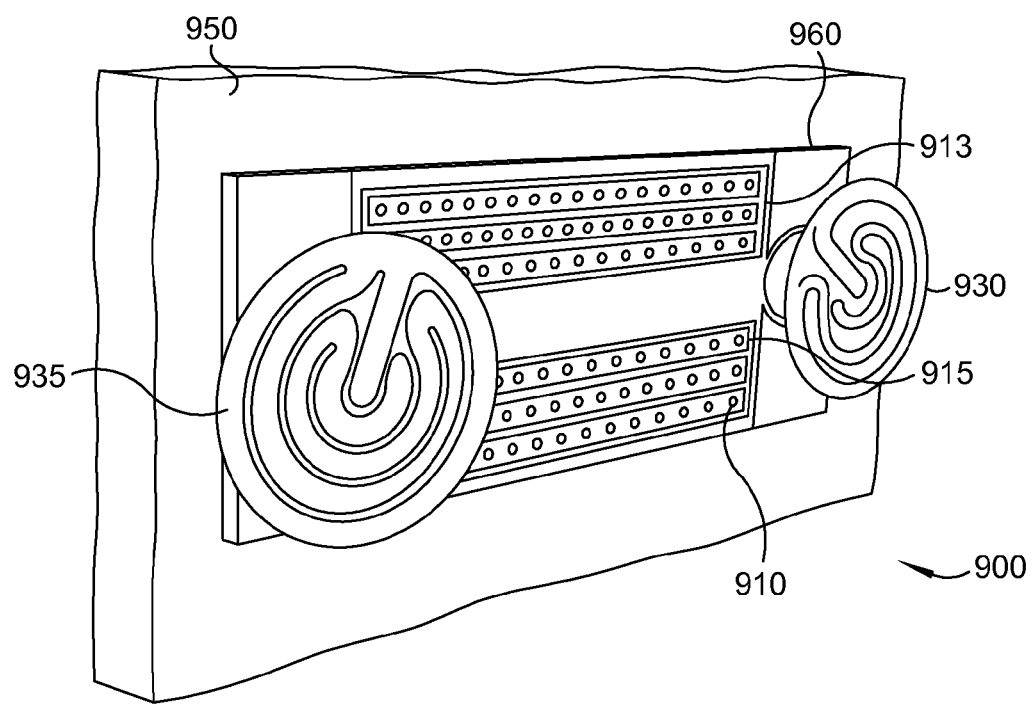
FIG. 9 is a view of an example IR emitter that may be employed as a heat source in the present invention.

FIG. 9 illustrates an example embodiment of an IR heat source that may be employed as a heat source in a sauna in accordance with the invention or for other heating applications. IR emitter 900 may include various combinations of IR emitters such as, for example, those discussed above in connection to FIG. 8, and preferably can be operated to emit IR over one or more desired wavelength-ranges and power-levels. In one embodiment IR source 900 may include a planar heating element 950 capable of providing far-IR, ceramic-based mid-IR emitters 930 and 935, and LEDs 910 capable of emitting near-IR. LEDs 910 may be arranged in a LED array 913 which may comprise one or more of a LED sub-array 915. IR source 900 may further include driver circuitry 960 for facilitating control of the IR emitters in accordance with the present invention. Specifically, driver circuitry 960 may comprise one or more individual driver modules and may be coupled to or operable to receive information from a heat control module, control panel, or a computing device. Each driver module may be configured to supply appropriate voltages or currents to some emitting elements or sub-arrays of elements needed for providing IR emissions, which correspond to specific wavelength-ranges or radiated output power-levels. For example, driver modules may be configured to use pulse width modulation for IR emitters, enabling more precise control over IR wavelength-ranges and radiated output power levels and thereby facilitating tuning IR heating. Driver circuitry may further include a printed circuit board wired to include an AC input voltage (Vcc), a DC gate voltage (Vg), and full-wave rectifier. LED sub-arrays may be coupled to Vg and optionally the rectifier in such a manner that the amount of current flowing into each sub-array may be controlled by varying Vg. In embodiments including a full wave rectifier, driver circuitry may further include components such as, for example, capacitors, operational amplifiers, and inductors for smoothing the output of the full-wave rectifier. Alternatively driver circuitry may be configured to pulse-operate the LED sub-arrays using the unsmoothed output of the rectifier. In this embodiment, the pulse width may be varied, for example, by changing the number of series-wired LEDs within each sub-array.

Figure 3:
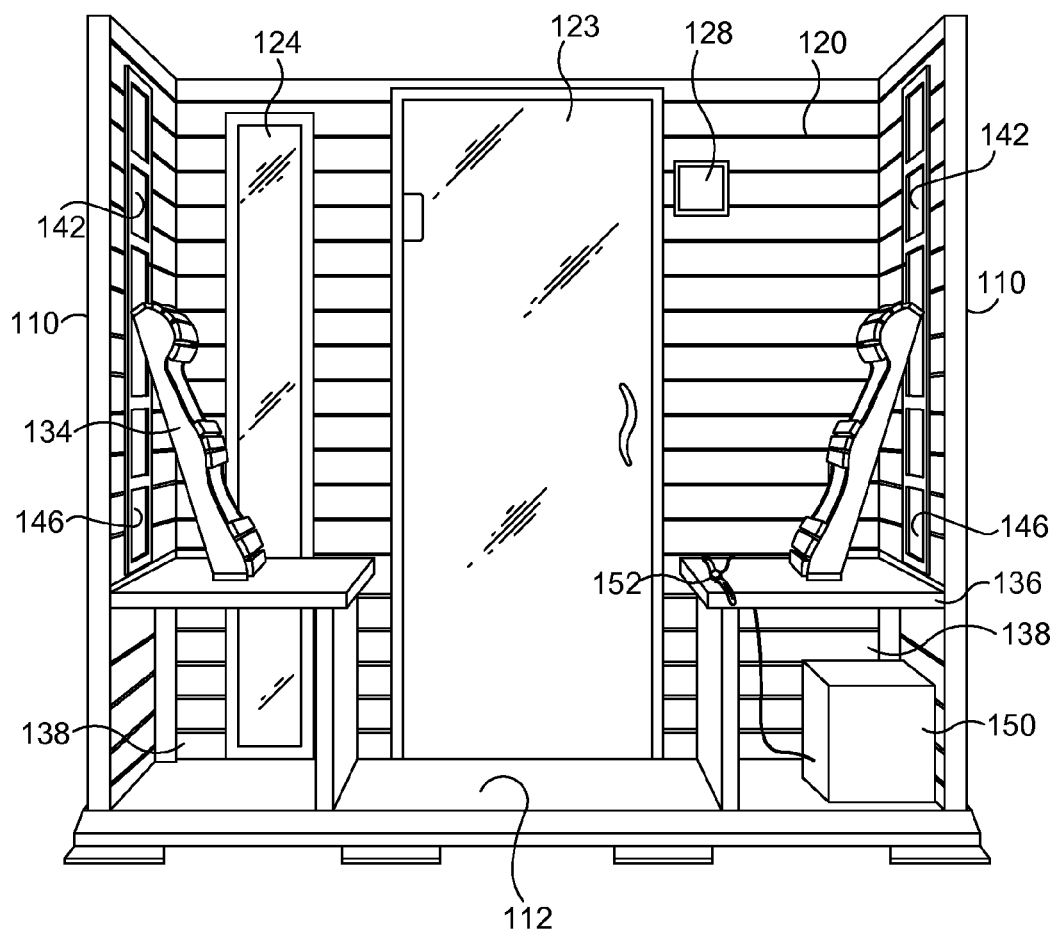
FIG. 3 is a cut-away rear view of a sauna in accordance with an embodiment of the present invention.

Turning now to FIG. 3, a forward-facing cut-away view of the interior of sauna 100 is illustrated. As indicated previously, sauna 100 may include an internal control panel 128 attached, for example, to an interior side of front panel 120. The interior control panel 128 may include any number of various control panels known in the art, such as, for example, configurations that include a number of buttons, dials, switches, and/or displays disposed thereon. In the embodiment illustrated in FIG. 3, the control panel 128 may include a display device such as, for example, a liquid crystal display (LCD) screen, a plasma display screen, or any other type of display screen appropriate for displaying various information associated with a user's sauna experience. In one embodiment, control panel 128 may comprise a touch-screen display device operable to display output as well as to receive user input, where a user may interact with control panel 128 by touching the screen with a finger, stylus, or other object. In still further embodiments, control panel 128 may be a portable device such as, for example, a remote control device or module. In other embodiments, control panel 128 may be adapted to be worn by a user, such as, for example, by affixing straps to a part of the body.

Control panel 128 may be integrated with, or coupled to, any of the various controllable features associated with sauna 100. For example, in an embodiment, control panel 128 is coupled to heat sources 140,142,144,146. In other embodiments, control panel 128 may be coupled to, and thus enable control of, other features such as adjustable lighting, timing devices, and the like.

In an embodiment, control panel 128 may be coupled to a multimedia entertainment system. A multimedia entertainment system may include audio devices, audio/video devices, and the like. For example, in an embodiment, a multimedia entertainment system may include such audio devices as a cd player, an MP3 player, or a connection for a portable music storage system such as an iPod®, available from Apple Incorporated of Cupertino, Calif. In other embodiments, audio devices may include or be interfaced with one or more receivers, speakers, etc. Multimedia entertainment systems may also include audio/video media devices such as televisions, monitors, projectors, DVD players, and the like. Multimedia content may be accessed by a multimedia system in any manner known in the art such as, for example, by accessing a storage device, by receiving transmissions, and the like.

In an embodiment of the present invention, a sauna may contain a multimedia therapeutic system, which may, for instance, be similar to a multimedia entertainment system, but may have therapeutic value (as compared with entertainment value). For example, in one embodiment, a sauna may be provided that includes Acoustic Resonance Therapy Products, such as the "SO SoundHeart" product line, available from So Sound Solutions, Inc., of Lafayette, Colo. In various other embodiments, multimedia therapy systems may include integrations of acoustic therapy products with therapy products that utilize lighting or other sensory effects.

Also illustrated in FIG. 3 is a monitoring device 152 that may be configured to collect biological data associated with a user of sauna 100. Monitoring device 152 may include a sensor and may be configured to communicate data collected by the sensor to a computing device such as, for example, computing device 150 described below. It will be readily appreciated by those skilled in the art that monitoring device 152 may be of any number of different configurations. In an embodiment, as illustrated in FIG. 3, monitoring device 152 may include a band that can be removably attached to a user's arm or wrist. In other embodiments, monitoring device 152 may include other sensor configurations as known in the art, and may include sensors that are disposed within the seating structure 136 or elsewhere within the enclosure of sauna 100.

In various embodiments, monitoring device 152 may communicate with a computing device 150. Computing device 150 may, as shown, be associated with the sauna. In other embodiments, computing device 150 is remote from the sauna, and may be located anywhere desired. For example, computing device 150 may be located at a doctor's office, a health club desk, a central serving station, a sauna manufacturer or retailer, or anywhere else desired. As used herein, computing device 150 may include, for example, client software adapted for communicating with a server. In other embodiments, computing device 150 may be a server.

In various embodiments, computing device 150 may be or include a control panel for controlling the sauna. In other embodiments, computing device 150 may be integrated with a control panel 128. In further embodiments, computing device 150 may be integrated with monitoring device 152. That is, computing device 150 may be part of monitoring device 152. In still further embodiments, computing device 150, monitoring device 152, and control panel 128 may all be integrated into a single device. It will be appreciated by those skilled in the art that any number of other components or devices may be integrated with any or all of computing device 150, monitoring device 152, and control panel 128.

Communication between monitoring device 152 and computing device 150 may be achieved using any communication technology known in the art. In some embodiments, communication may be achieved, for example, using radio technology, Bluetooth™ technology, infrared technology, 802.11 technology, USB™ ports, Firewire® ports, analog phone lines, etc.

Monitoring device 152 may be configured to collect biological data associated with a user of sauna 100. In an embodiment, such biological data may include, for example, measurements or other information corresponding to a user's blood pressure, heart rate, core body temperature, perspiration rate, and the like. In another embodiment, biological data may include a user's body weight. In a further embodiment, biological data may include data regarding a user's breathing performance such as, for example, a breathing rate or blood oxygen saturation. In still further embodiments, biological data may include any data commonly collected during a stress test, which may be performed using a particular wavelength of the exit.

It will be appreciated by those skilled in the art that monitoring device 152 can be configured to collect information regarding these and many other data associated with a physiological state of a sauna user. In some embodiments, for example, monitoring device 152 may comprise one or more sensors that can be attached to various parts of a user's body for collecting and/or rendering data such as data associated with common tests like EEGs or EKGs. In other embodiments, monitoring device 152 may be adapted for measuring breathing rates, lung capacity, or compositions of exhaled air. These data may be used, for example, in performing wellness analyses, preparing training programs, and tracking user progress, as described further below.

Both the monitoring device 152 and the control panel 128 may be configured to communicate with a computing device 150. In another embodiment, computing device 150 may be integrated with control panel 128 as a single device. In further embodiments, any one or combination of monitoring device 152, control panel 128, and computing device 150 may be a single device or multiple devices. As shown in FIG. 3, computing device 150 may be situated in an open space 138 underneath a seating structure 136, as described above. In other embodiments, computing device 150 may be situated in any other region of the enclosure. In further embodiments, computing device 150 may be attached to an outside surface of sauna 100. In still further embodiments, computing device may not be attached to sauna 100, but rather be separate from sauna 100. For example, computing device 150 may be situated nearby sauna 100 or may be in a remote location, such as, for example, near a front desk of a health club. In still further embodiments, one or more components of computing device 150 may be situated in one location with other components situated in other locations.

Computing device 150 may communicate with other devices, with features associated with the sauna, with monitoring device 152, and with control panel 128 in any manner known in the art. For example, in one embodiment, communication cables such as USB cables or fiber-optic cables may be used to facilitate communication. In other embodiments, communication may be achieved using wireless technology. In further embodiments, communication may be indirect such as, for example, in the case where a user wishes to extract some piece of data or information from the computing device 150 for storage or transport to another device. Accordingly, computing device 150 may include a USB port or other type of input/output mechanisms such as disk drives, external portable hard drives, discs. These embodiments are presented only as examples of possible configurations, and are not intended to limit the placement of computing device 150 or any other device or feature described herein.

The computing device 150 may be provided for controlling the operation of the sauna 100, or any aspect or combination of aspects of the operation of sauna 100. In some embodiments, the computing device includes an independent computing device dedicated to the sauna 100. In other embodiments, the computing device 150 may be the control panel 128 or a component of the control panel 128. The computing device may receive inputs, such as inputs associated with temperature settings, light settings, and biological data. Based on the inputs, the computing device may control the sauna features within the enclosure. For example, computing device 150 may adjust the lighting level, temperature, or other aspects of operation of the sauna 100, based upon criteria such as a timed program, collected biological data, inputs received from a user, etc. The computing device 150 may include various input/output devices or components such as, for example, printers, displays, etc. The computing device 150 may also include one or more connection ports for providing interfaces with peripheral devices such as storage devices, other computing devices, additional monitors, multimedia entertainment devices, adjustable lighting devices, etc.

In some embodiments, the computing device may act as a stand-alone device such that the computing device maintains all data necessary for operating the features of the sauna 100. In other embodiments, however, the computing device operates within a distributed computing environment. In one embodiment, the computing device may be interfaced with or integrated into, for example, a computing system. The computing system may be a comprehensive computing system within a networking environment such as the exemplary computer network environment 400 shown in FIG. 4. It will be understood and appreciated by those of ordinary skill in the art that the illustrated computer network environment 400 is merely an example of one suitable computing environment and is not intended to suggest any limitation as to the scope of use or functionality of the invention. Neither should the computer networking environment 400 be interpreted as having any dependency or requirement relating to any single component or combination of components illustrated therein.

Embodiments of the present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, mini-computers, mainframe computers, distributed computing environments that include any of the above-mentioned systems or devices, and the like.

Embodiments of the present invention may be described in the general context of computer-executable instructions, such as program modules, being executed by a computer. Generally, program modules include, but are not limited to, routines, programs, objects, components, and data structures that perform particular tasks or implement particular abstract data types. Embodiments of the present invention may also be practiced in distributed computing environments where tasks are performed by remote processing devices that are linked through a communications network. In a distributed computing environment, program modules may be located in local and/or remote computer storage media including, by way of example only, memory storage devices.

Figure 4:
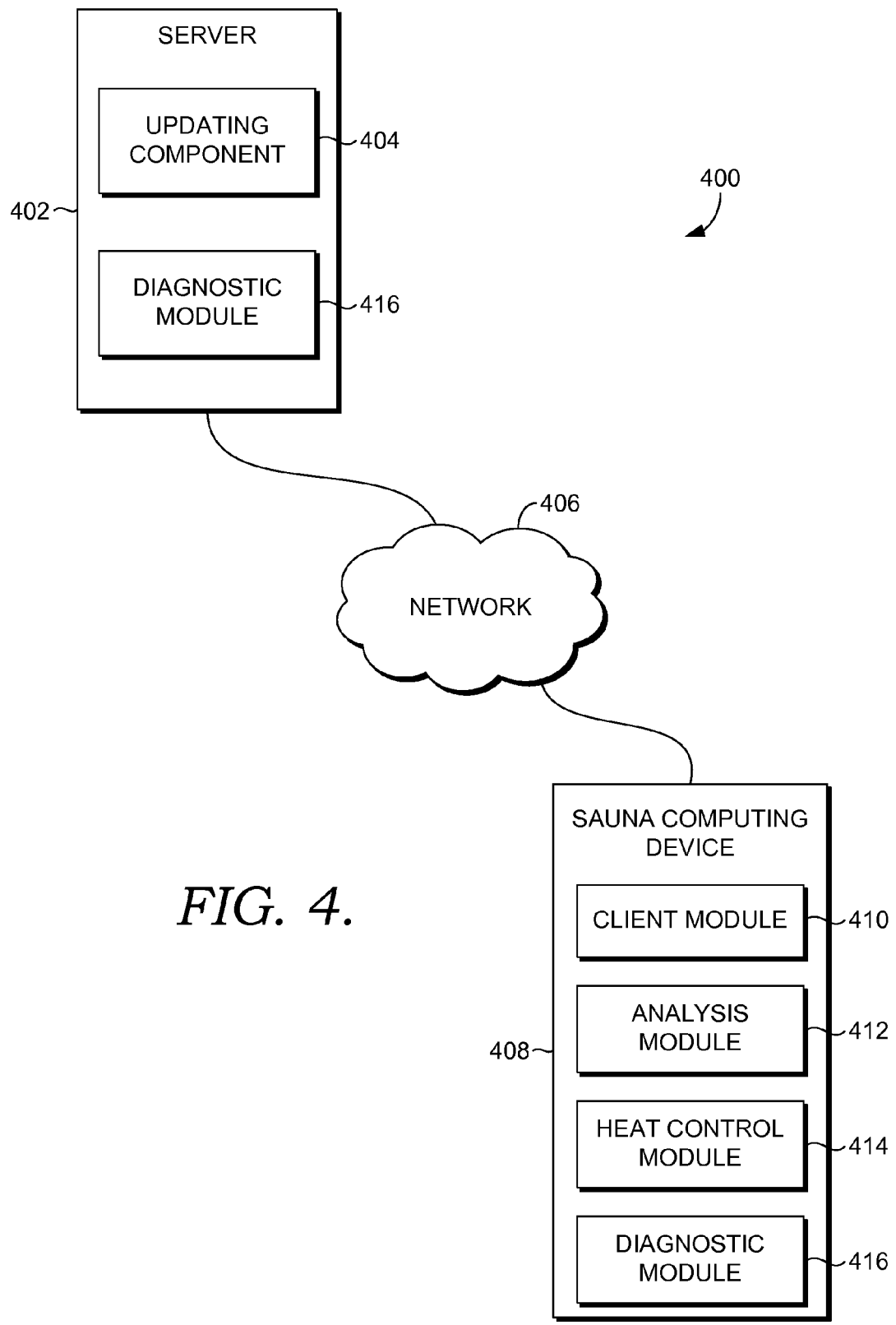
FIG. 4 is a block diagram of an exemplary computing environment suitable for use in implementing the present invention.

With continued reference to FIG. 4, the exemplary computer networking environment 400 includes a general purpose computing device in the form of a server 402. Server 402 may be remote from the computing device 150 described above or server 402 may be computing device 150. Components of the server 402 may include, without limitation, a processing unit, internal system memory, and a suitable system bus for coupling various system components with the server 402. The system bus may be any of several types of bus structures, including a memory bus or memory controller, a peripheral bus, and a local bus, using any of a variety of bus architectures. In one embodiment, two or more servers may be directly or indirectly connected to each other without using network 406. While the server 402 is illustrated as a single unit in FIG. 1, one skilled in the art will appreciate that the server 402 is scalable. The server 402 may in actuality include any number of servers in communication. For example, in one embodiment server 402 may actually include two servers, and in another embodiment server 402 may be a bank of servers. The single unit depictions are meant for clarity, not to limit the scope of embodiments in any form.

The server 402 typically includes, or has access to, a variety of computer readable media. Computer readable media can be any available media that may be accessed by server 402, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 402. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The server 402 may operate in a computer network 406 using logical connections to one or more computing devices 408. Computing devices 408 may be located at a variety of locations such as, for example, in a health club, office, spa, clinical, or home environment. Computing devices 408 may, in some embodiments, be operable to control various features within saunas as described throughout this document. In other embodiments, computing devices 408 may be centrally located and be operable to control a plurality of saunas, and may, in addition, be configured to perform various other functions. The computing devices 408 may be personal computers, servers, routers, network PCs, peer devices, other common network nodes, or the like, and may include some or all of the components described above in relation to the server 402. The devices can be personal digital assistants or other like devices.

Exemplary computer networks 406 may include, without limitation, local area networks (LANs) and/or wide area networks (WANs). Such networking environments are commonplace in offices, and may include such embodiments as enterprise-wide computer networks, intranets, and the Internet. When utilized in a WAN networking environment, the server 402 may include a modem or other means for establishing communications over the WAN, such as the Internet. In a networked environment, program modules or portions thereof may be stored in the server 402 or on any of the computing devices 408. For example, and not by way of limitation, various application programs may reside on the memory associated with any one or more of the computing devices 408 or servers 402. It will be appreciated by those of ordinary skill in the art that the network connections shown are exemplary and other means of establishing a communications link between the computers (e.g., server 402 and computing devices 408) may be utilized.

In operation, a user may enter commands and information into the server 402 or convey the commands and information to the server 402 via one or more of the computing devices 408 through input devices, such as a keyboard, a pointing device (commonly referred to as a mouse), a trackball, touchscreen, or a touch pad. Other input devices may include, without limitation, microphones, satellite dishes, scanners, or the like. Commands and information may also be sent directly from a remote sauna to the server 402, as well as from server 402 to any number of remote saunas. In addition to a monitor, the server 402 and/or computing devices 408 may include other peripheral output devices, such as speakers and a printer.

Server 402 may also be configured to receive diagnostic information from another computing device, such as computing device 408. In other embodiments, server 402 may maintain a website or other publicly or privately viewable collection of information. A website maintained by server 402 may include interactive information for users, updates for sauna feature settings, information regarding saunas, interactive repair services, and any other feature, service or set of information that may be helpful or necessary in accomplishing any of the other objects, embodiments, processes, and environments described herein with respect to the present invention.

Figure 5:
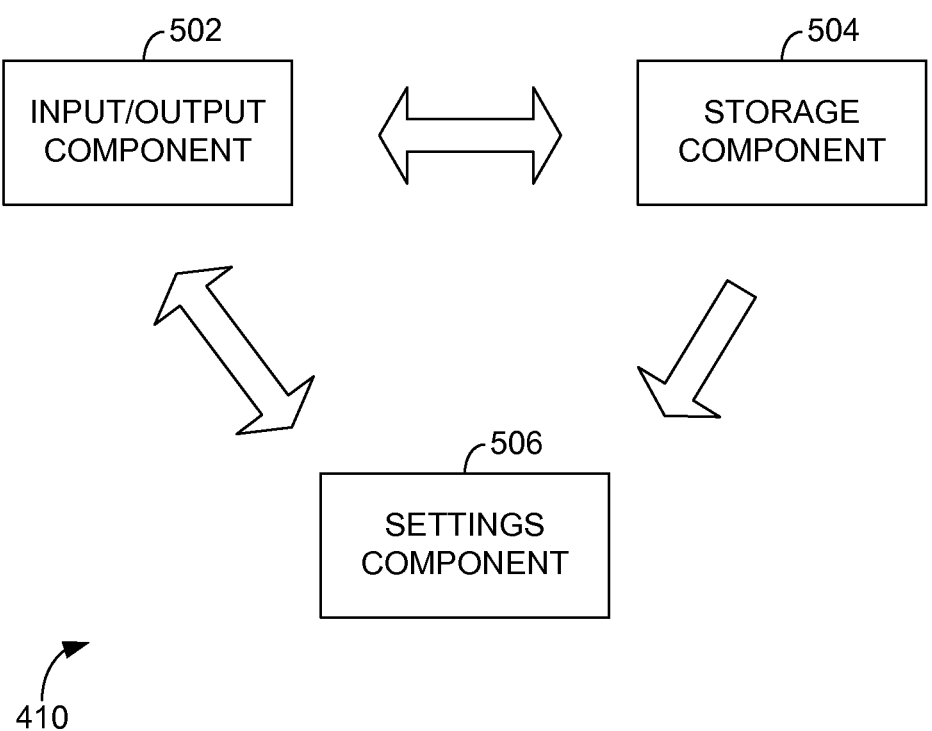
FIG. 5 is a block diagram showing an exemplary client module in accordance with an embodiment of the present invention.

As illustrated in FIG. 4, computing device 408 may include a client module 410 that facilitates, in part, communications between the computing device 408 and server 402. For example, turning briefly to FIG. 5, a schematic illustration of an exemplary client module 410 is shown. As illustrated, client module 410 may include an input/output component 502 for communicating with a server 402. The input/output component 502 may be configured to send communications to server 402, as well as receive communications from server 402. In one embodiment, for example, the input/output component may facilitate communicating data such as biological data to server 402. In an embodiment, input/output component 502 may be configured to receive communications including sauna feature settings from server 402.

As used herein, a sauna feature setting may include any setting or configuration that, when applied to a device or feature associated with a sauna, provides a particular experience to a sauna user. For example, in an embodiment, a sauna feature setting may include a temperature or wavelength setting that, when applied via computing device 408 to a heat source included in a sauna, results in the heat source emitting a particular amount of heat or radiation at a particular wavelength. In other embodiments, a sauna feature setting may correspond to such features as adjustable lighting, wherein applying a sauna feature setting may cause a particular type of lighting effect or ambience within the enclosure.

In further embodiments, a sauna feature setting may be associated with any number of other features of a sauna such as, for example, a timer device that is operable to control the duration of heat output at particular wavelengths, settings internal to computing device 408, entertainment media devices (e.g. audio, visual, or audio/visual media presentation devices), and monitoring devices, such as described above. In embodiments of the present invention, sauna feature settings may be saved individually or in combination with other sauna feature settings. In various embodiments, saved or stored sauna feature settings may correspond to certain types of treatment, certain users, or recently used settings. Saved sauna feature settings may be organized, in an embodiment, into one or more profiles associated with users, treatment types, or any other desired factor, parameter, or event.

Sauna feature settings may be defined by a sauna user, a health club operator, or a computer program and may be applied to the sauna in any number of ways such as by inputting the sauna feature settings via a control panel such as the control panel 128 illustrated in FIG. 3, a computing device 408, or a server 402. In this regard, server 402 may include a dynamic experience updating module 404, as illustrated in FIG. 4. The updating module 404 may be configured to generate sauna feature settings to be communicated to and applied by a computing device 408. The updating module may, for example, receive data from the client module 410 that may include biological data associated with a user, and use this data to generate appropriate sauna feature settings that provide an optimum experience for the user. These sauna feature settings may be generated and applied during a sauna session, that is while a user is using the sauna, or may be generated and/or applied before or during a later session.

In an embodiment, the updating module 404 is configured to work with the client module 410 of the computing device 408 in order to maintain a training program. A training program may include a program such as those known in the art to be associated with any number of various health or fitness programs such as, for example, workout programs, aerobics programs, and the like. A sauna training program may also include programmed settings for achieving, for example, such health benefits as detoxification of a user's body or weight loss. It will be readily appreciated by those skilled in the art that the potential benefits from controlled heating environments such as saunas are numerous.

A training program may include a number of predetermined progress levels that correspond to various sauna feature settings. A user may utilize such a training program by engaging in sauna sessions at a particular progress level, and upon successfully completing a progress level, moving on to another progress level that corresponds to different sauna feature settings. In this manner, biological data associated with the physiological response of a user to sauna sessions may be logged, analyzed, and tracked in order to vary the sauna experience in a manner that facilitates achieving optimal health, comfort, and therapeutic benefits from the use of the sauna.

In other embodiments, updating module 404 may be configured to manage user profile settings. A user profile may include various settings related to sauna features such as those described above. A user profile may contain settings directed toward specific comfort levels, experience types, and users.

Returning to FIG. 5, client module 410 may also include a storage component 504 for storing data such as, for example, biological data collected by a monitoring device such as the monitoring device 152, illustrated in FIG. 3. The storage component 504, shown in FIG. 5, may further be configured to store any other type of data or information, including data and information associated with a training program, as described below. Client module 410 may further include a settings component for facilitating the application of sauna feature settings to the various features, devices, and aspects of a sauna.

Returning now to FIG. 4, computing device 408 may also include an analysis module 412 for analyzing data and information. Various data and information may be received by the analysis module 412 from any number of sources, such as the client module 410, a control panel, or a monitoring device such as the monitoring device 152 described above. The analysis module 412 may be configured to perform any number of various analysis processes on data and/or information received therein. Module 412 may be integral to sauna, or may be external to sauna—for example, associated with a web server or other external computer. In an embodiment, analysis module 412 is configured to analyze biological data collected by a monitoring device such as monitoring device 152 described above. Analysis module 412 may generate, as output, any number of types of data and/or information that may be represented in any manner known in the art such as, for example, values, graphs, tables, and charts. In other embodiments, analysis module 412 may output information to another device such as a computing device, diagnostic device, control panel, etc. In an embodiment, such information may be outputted to a webpage where it can be managed and viewed by a user or others. In other embodiments, information may be outputted to a server or storage system for various purposes. In an embodiment, analysis module 412 may be configured to determine various factors associated with a user's physiological health or response to a sauna experience. Such information may include, but is not limited to, computations related to energy such as caloric measurements.

Computing device 408 may also include a heat control module 414 for controlling and adjusting the various outputs of heat sources within the sauna. The heat control module 414 may be configured to implement heat or wavelength settings as inputted by a user or other device. In one embodiment, heat control module 414 includes a timing mechanism for controlling the length of time that heat sources produce output. In another embodiment, heat control module 414 may be configured to cause the sauna to rapidly achieve a desired temperature such as by, for example, causing the heat sources to generate a higher heat output for a period of time before a user enters the enclosure. Additionally, computing device 408 and/or server 402 may include a diagnostic module 416 for performing diagnostics associated with the operation of the sauna. It will be readily appreciated by those skilled in the art that a sauna having controllable features and devices therein generally includes one or more electrical systems for facilitating the operation and control of those features and devices. Such an electrical system may include any number of circuits and may be operable to transmit electricity to and from features and devices. An electrical system may be configured to be generally used for providing power or transferring information.

Diagnostic module 416 may be configured to communicate with one or more diagnostic devices disposed within the sauna enclosure. In other embodiments, diagnostic module 416 may be configured to communicate with other modules associated with a computing device within the sauna. In further embodiments, diagnostic module 416 or diagnostic devices may be configured to communicate with other remote computing devices, diagnostic devices, or software modules. For example, in an embodiment, diagnostic module 416 may be configured to communicate diagnostic information and error reports to a repair service provider without interaction from a user. In still further embodiments, diagnostic module 416 may be configured to prepare repair requests and/or order replacement parts, with or without input from the user and may even be configured to perform various tasks such as these without the user ever knowing about it.

The diagnostic devices may be coupled to different locations within the various circuits that comprise the electrical systems of the sauna. This way, the diagnostic devices may be configured to monitor the flow of electricity through various channels in the electrical system and may be further configured to detect and gather data associated with electrical failures. In an embodiment, the diagnostic device may also be configured to test circuits such as by applying a signal to a circuit. As used herein, an electrical failure may be any undesired or unexpected event within the electrical system that results in the performance of the electrical system being anything other than the performance for which the electrical system is designed.

Upon detecting an electrical failure, the diagnostic devices may communicate information and/or data associated with the electrical failure to the diagnostic module 416. The diagnostic module 416 may be configured to analyze such data in order to determine various characteristics associated with the electrical failure such as what the electrical failure consists of, what caused the electrical failure, how the electrical failure will or does affect other aspects of the electrical system, and how to repair the electrical system to eradicate the effects of the electrical failure. In various embodiments, the diagnostic module 416 may be configured to output diagnostic information on a display device, to send diagnostic information to a remote location such as to a server, or output diagnostic information in any other manner known in the art.

Figure 6:
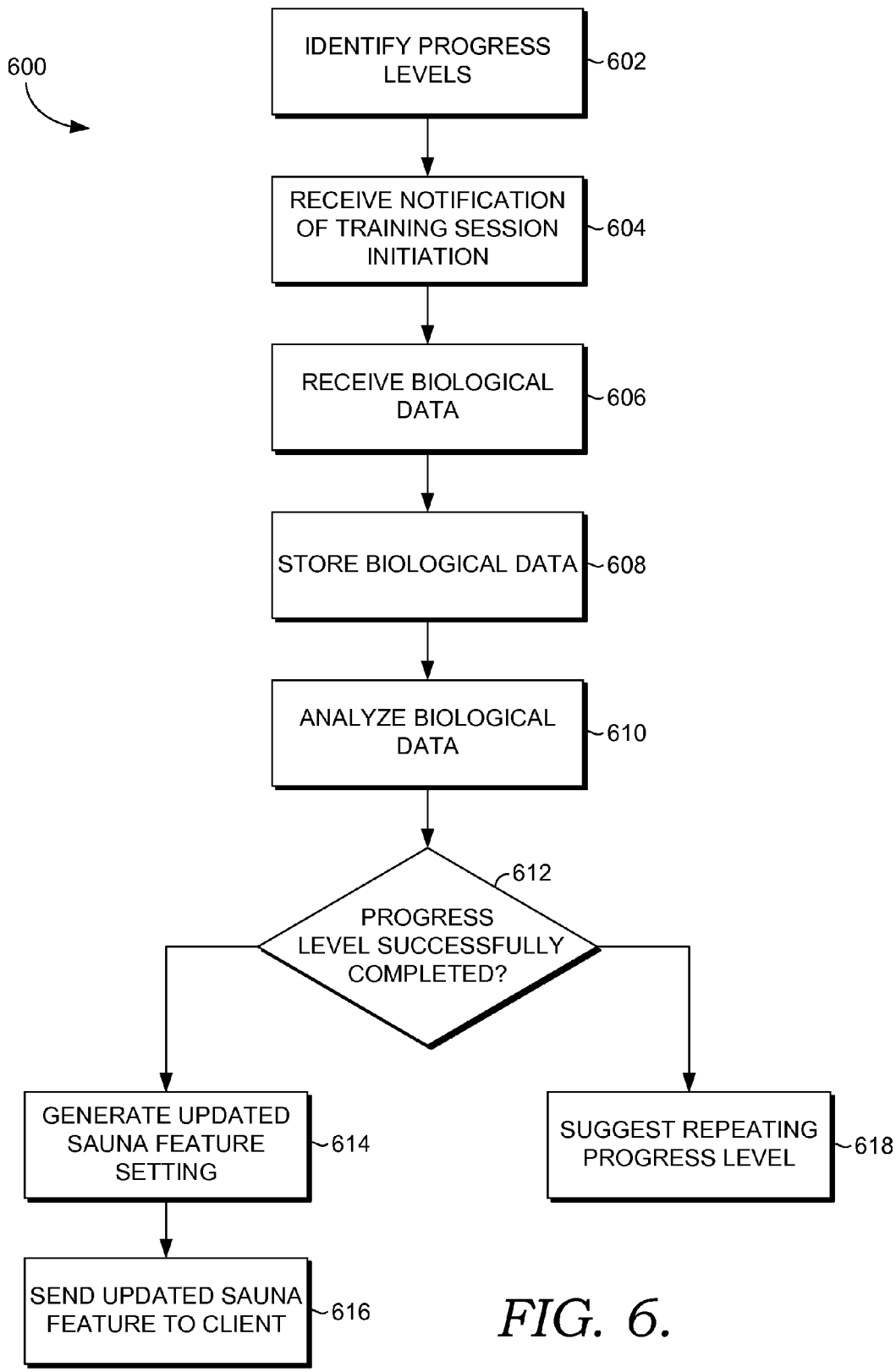
FIG. 6 is a flow diagram showing a method for using a sauna in accordance with an embodiment of the present invention.

Turning to FIG. 6, a flow diagram is provided that shows a method 600 for using a sauna in accordance with an embodiment of the present invention. In an embodiment, a training program such as that described above may be maintained and managed at a server such as server 402 illustrated in FIG. 4. At step 602 of FIG. 6, a plurality of progress levels associated with a training program are identified. As indicated above, each of these progress levels may correspond to one or more sauna feature settings such as, for example, duration of a training session, temperature of various heat sources in various zones, radiation wavelengths emitted by heat sources in various zones, humidity levels, and the like.

In various embodiments, progress levels may be designed for training programs targeted to specific types of users, therapy, illnesses, conditions, injuries, locations, etc. For example, in one embodiment, a training program may be designed with sauna feature settings selected for use by users of a certain age, gender, health status, or the like. In an embodiment, for example, a training program may be designed especially for pregnant women. In another embodiment, a training program may be designed for women with fibromyalgia who are older than 40 years old. These are but a few examples of a myriad of possibilities and are not intended to limit the purposes for which a training program may be designed in any way.

At step 604, notification is received that indicates that a user has initiated a training session associated with a first one of the progress levels. As the training session progresses, biological data associated with the user is received at step 606 from a client, such as client module 410 of computing device 408 as illustrated in FIG. 4.

As illustrated at step 608, the biological data is stored after being received. In an embodiment, the biological data may be stored as part of a session entry in a training log associated with the user. At step 610, the biological data is analyzed in order to generate conclusions regarding the user's wellness and physiological responses to the training session. This analysis is used at the end of the training session to determine, in step 612, whether the user has successfully completed the progress level. If the user has successfully completed the progress level, sauna feature settings corresponding to the next progress level are generated, as shown at step 614. These feature settings are communicated to the client at step 616.

Figure 7:
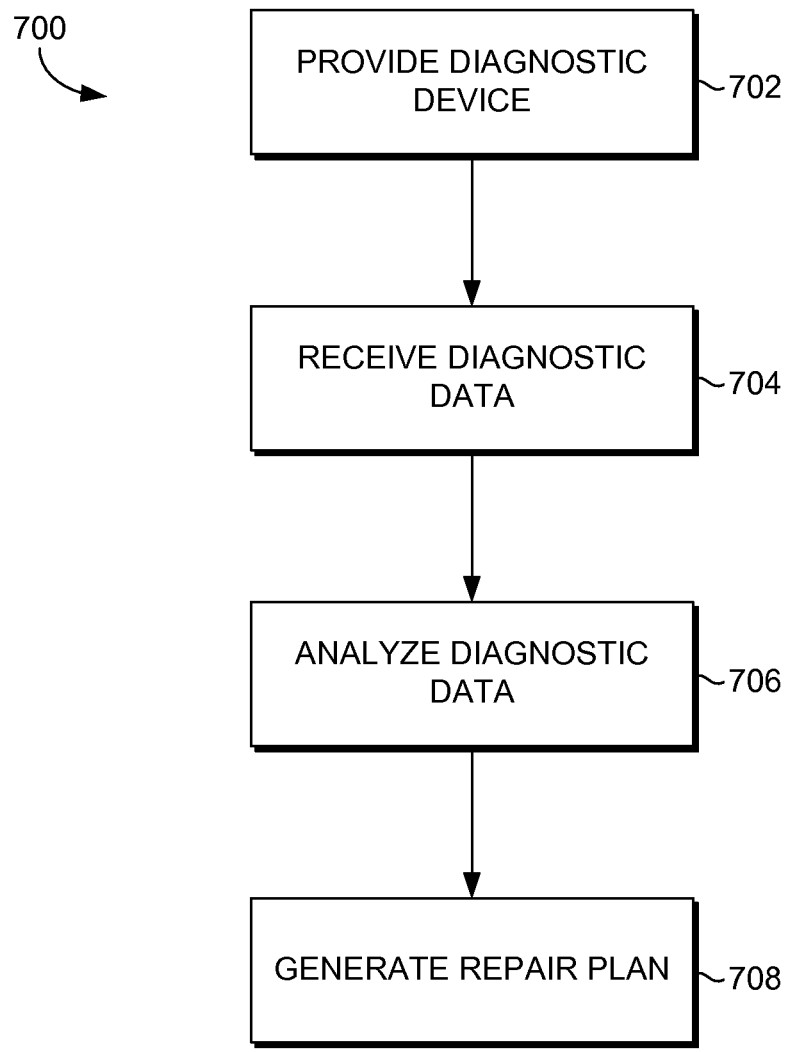
FIG. 7 is flow diagram showing a method for using a sauna in accordance with an embodiment of the present invention.

Turning now to FIG. 7, another flow diagram is shown illustrating a method 700 of using a sauna according to an embodiment of the present invention. As shown in FIG. 7, step 702 consists of providing diagnostic devices for detecting electrical failure within one or more of the various electrical systems associated with a sauna. At step 704, diagnostic data are received from the diagnostic devices. This diagnostic data, as explained above, may relate to any number of aspects of an electrical failure.

The diagnostic data is analyzed at step 706 to determine characteristics associated with the electrical failure. Based on the results of this analysis, a repair plan is generated at step 708. The repair plan may include a set of instructions or recommendations corresponding to actions that can be taken, either by an individual or by a system device, to remedy the problem or problems that resulted in the electrical failure.

Figure 10A:
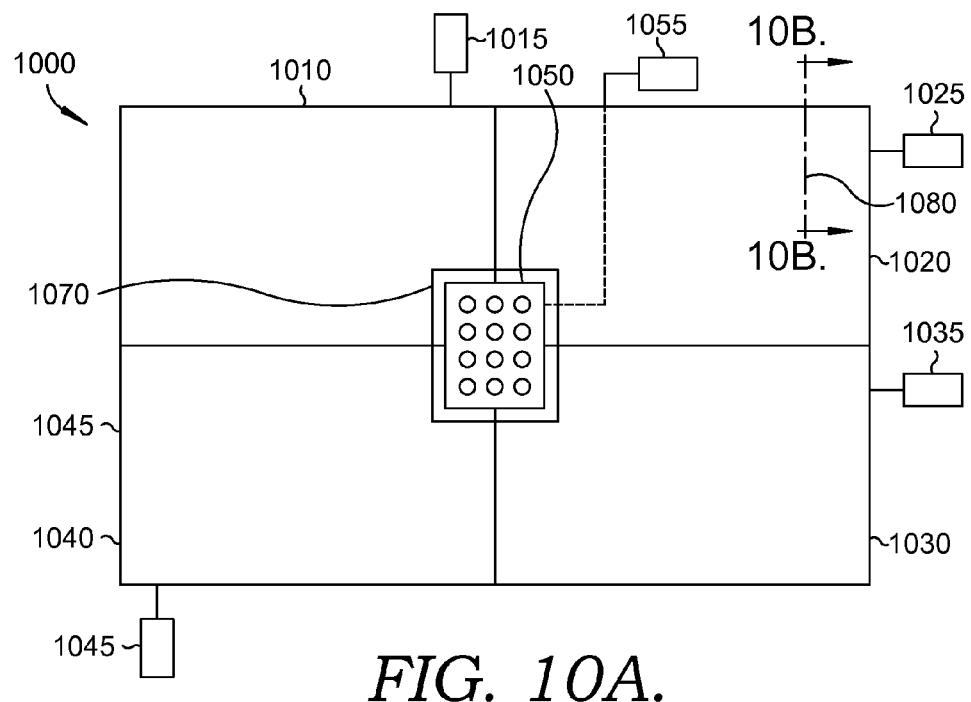
FIG. 10A is a view of an exemplary IR source in accordance with the present invention.

Referring now to FIG. 10A, an infrared source 1000 in accordance with the present invention is illustrated. Infrared source 1000 may comprise a plurality of sections, such as first section 1010, second section 1020, third section 1030, and fourth section 1040. Each section may comprise an electronically discreet heating element. A heating element may be, for example, a flexible high-resistance polyimide material that may be tuned to emit infrared radiation with a peak emission wavelength at a selectable wavelength. A high emissivity coating may cover the surface of the polyimide substrate, if desired.

Figure 10B:
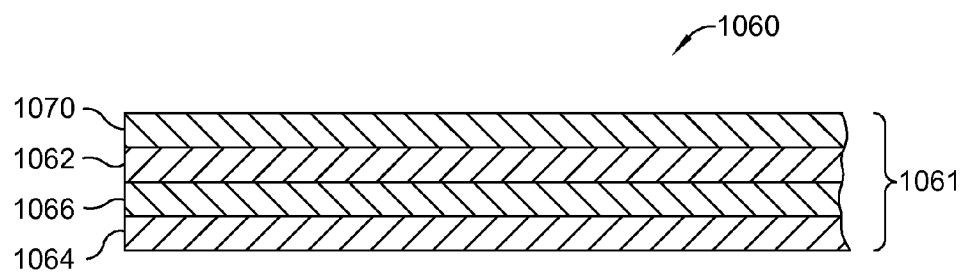
FIG. 10B is a cross-sectional view of one exemplary IR heat source in accordance with the present invention.

Further details of a polyimide heater element, such as may be used for first heater element 1010, second heater element 1020, third heater element 1030, and/or fourth heater element 1040, are illustrated in FIG. 10B. FIG. 10B illustrates a cross-sectional view of a polyimide heater element 1060 that comprises a substrate 1061. Substrate 1061 may comprise a first polyimide layer 1062 and a second polyimide layer 1062, with a metallic foil 1066 between first polyimide layer 1062 and second polyimide layer 1064. First polyimide layer 1062 and second polyimide layer 1064 may be approximately 0.002 inches thick. Metallic foil 1066 may comprise copper foil approximately 0.005 inches thick. Metallic foil 1066 may be etched with conducting traces. Metallic foil 1066 may effectively reduce inductance and EMI. High emissivity coating 1070 may be applied to the surface of the substrate 1061 intended to face the subject/object to be heated. High emissivity coating 1070 may comprise, for example, Insuladd® suspended in matt black paint, resulting in an estimated emissivity of 0.98. Of course, any type of high emissivity coating may be used. For example, various non-metallic plastics high temperature paints such as Thurmalox by Dampney Engineering Coatings, and/or powder coatings may be used as high emissivity coating 1070. While the substrate 1061 illustrated in FIG. 10B comprises a first polyimide layer 1062, a metallic foil 1066, and a second polyimide layer 1064, other substrates may be used. For example, substrate 1061 may comprise Cirlex, which is a proprietary, all polyimide material, comprising layers of DuPont Kapton®. If used, Cirlex may comprise a thickness of from about 0.008 inches to 0.125 inches. By way of further example, substrate 1061 may comprise etched foil or wound wire between layers of fiberglass reinforced silicone rubber. Yet a further example of a substrate 1061 is an etched foil layer between layers of mica. Of course, further types of materials may be used for substrate 1061 without departing from the scope of the present invention.

Referring again to FIG. 10A, one of skill in the art will further realize that sections as illustrated in FIG. 10 may comprise various types of heating elements illustrated in FIG. 8. As illustrated in FIG. 10, first section 1010 may be controlled using a first thermocouple 1015, second section 1020 may be controlled using a second thermocouple 1025, third section 1030 may be controlled using a third thermocouple 1035, and fourth section 1040 may be controlled using a fourth thermocouple 1045. The use of thermocouples may be advantageous in providing a finer control of the radiative temperature of the section it controls than a thermostat, but a thermostat or other type of control device may be utilized. As illustrated in FIG. 10, infrared source 1000 may further comprise an additional heating zone 1050 controlled by a fifth thermocouple 1055, although other types of heat control devices may be used. As illustrated in FIG. 10, fifth heating zone, 1050 comprises an LED array. For example, LED array 1050 may emit far-infrared radiation under the control of thermocouple 1055. As illustrated in FIG. 10, different types of emitters may be used in combination to provide different types of infrared spectrum simultaneously. For example, first section 1010 may be set (by the user, by an administrator, by a software program, or by other sources) to emit infrared radiation in the near-infrared spectrum. Meanwhile, second heater section 1020 and third heater section 1030 may be set (by similarly various means as the first section 1010) to emit infrared radiation in the mid-infrared spectrum. Fourth section 1040 may be deactivated for purposes of a given infrared application. Meanwhile, fifth section 1050 may be activated (similarly to first section 1010) to emit infrared radiation in the far-infrared portion of the spectrum. One of skill in the art will appreciate that any given peak infrared wavelength will correspond to a surface temperature of the emitting heater section. In such a fashion, a user may obtain a spectrum having a desired peak or peaks of infrared radiation at one or more desired wavelengths, as well as a peak desired power of radiation. While infrared sources such as IR source 1000 may be particularly useful in saunas, as described herein, one of skill in the art will appreciate that a tunable infrared source such as IR source 1000 may be useful in a number of applications.

Overall, infrared source 1000 may be approximately 25.5 inches long and approximately 13.5 inches high. Fifth heating section 1050 may comprise approximately a 4 inch by 6.5 inch section approximately centered within infrared source 1000. A space 1070 of approximately 1 inch may be provided between fifth heating section 1050 and first heating section 1010, second heating section 1020, third heating section 1030, and fourth heating section 1040 to facilitate the operation of fifth heating section 1050 at a lower operating temperature than first heating section 1010, second heating section 1020, and third heating section 1030, and fourth heating section 1040. The power density of one or more section of infrared source 1000 may be selected based upon the cooling load of the heating section. The desired power density may impact the shape and density of copper traces in the polyimide heater example illustrated in FIG. 10B. For sauna applications, in which the cooling load may be limited air in contact with the heating section, a desirable power density may be 2.5 w/in$^2$ at 120 Vrms. Individual heating elements of infrared source 1000 may, optionally, be thermal limited to a maximum surface temperature of 160° C. If fifth heating section 1050 is an LED array, a resistor, such as a 26Ω drive resistor may be used to limit current to the LED array. The drive resistor, being a current limiting mechanism, may dissipate excess energy through ohmic heat loss. The drive resistor may be integrated directly onto a polyimide heating layer as an appropriately sized metallic trace.

Figure 11:
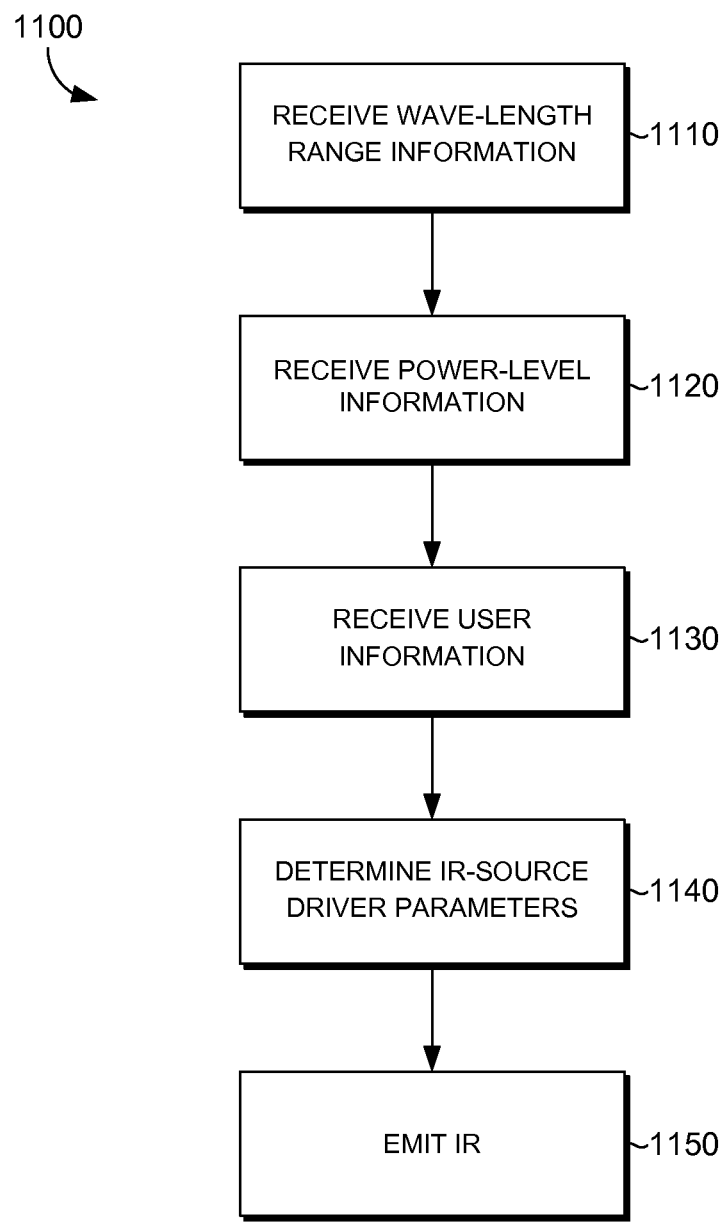
FIG. 11 is a method by which an embodiment of the present invention may be used for tuning IR heating in a sauna.

Turning now to FIG. 11, another flow diagram is shown illustrating an example embodiment of a method 1100 for tuning IR heating in a sauna. At step 1110, wavelength-range information is received. This information relates a portion of the infrared spectrum and may come from a control panel or computing device. It may be provided by a user or computing device. For example, a user may select settings with a control panel or heat control module indicating desired IR wavelength ranges. One of skill in the art will appreciate that a user may select wavelength information either directly or indirectly. For example, a user may directly select a specific wavelength(s) (for example, ten microns) or a specific range of wavelengths (for example, near-infrared). Alternatively, a user may indirectly select a wavelength(s) by selecting a sauna program (for example "Detox"). Alternatively a computing device may provide information relating to wavelength-ranges based on, for example, biological data of a user, program settings built into the sauna, information provided by a health club, or other available information. At step 1120, power-level information is received. This information relates to radiated power output levels of IR emitted at wavelengths corresponding to the wavelength-ranges received at step 1110. Power-level information may be received from the same sources and be provided in a similar manner as the wavelength-range information. For example, power-level information may be selected directly or indirectly by a user. Alternatively, power-level information may be received from driver circuitry of IR emitting sources. At step 1130, user information is received This information may include information related to specific locations on one or more users' bodies or specific pains, conditions, or symptoms associated with users. User information may be received from the same sources and be provided in a similar manner as the wavelength-range information. For example, user information may be received directly or indirectly from a user. Step 1140 determines parameters for IR-source drivers based on the received information. This may include determining any control instructions; control signals; and specific voltage or current levels; including gate voltages duty-cycles, pulse-widths, or pulse-width-modulation frequencies, for example, for facilitating emission of IR corresponding to the received wavelength-range information, power-level information, and user information. Finally, at step 1150, IR is emitted, from one or more infrared sources, at wavelength-ranges and power-levels corresponding to the received information. Furthermore in one illustrative embodiment, the emitted IR may be directed to specific locations on a user's body corresponding to the received user-information. Step 1150 may be performed by selectively activating IR sources and/or selectively activating IR elements within a given IR source. For example, only the far-infrared emitting elements in the IR source near a user's legs may be activated, while both the near- and mid-infrared emitting elements in the IR source(s) near a user's torso are activated, while none of the infrared emitting elements in the IR source(s) near a user's head are activated. Of course, such a selective activation may employ any degree of spatial, temporal, power, and/or wavelength specificity desired in constructing a sauna in accordance with the present invention.

Figure 12:
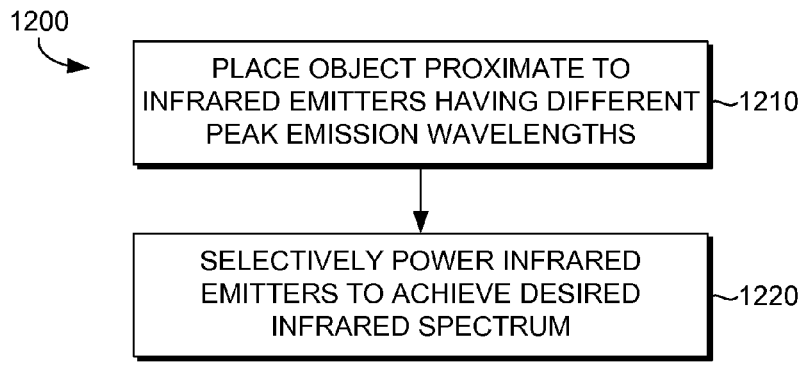
FIG. 12 is a further method in accordance with the present invention.

Referring now to FIG. 12, a further method 1200 in accordance with the present invention is illustrated. In step 1210 an object may be placed approximate to infrared emitters having different peak emission wavelengths. The emitters having different peak emission wavelengths as referenced in step 1210 may possess inherently different peak emission wavelengths, such as may be the case for emitters constructed of different materials that inherently emit at a different wavelength than one another, or may utilize tunable emitters that may be tuned to emit at differing peak wavelengths. Further, step 1210 may utilize a combination of tunable and non-tunable emitters. In step 1220 the infrared emitters are selectively powered to achieve a desired infrared spectrum. This spectrum will ultimately be radiated to the object, which may comprise a human body if method 1200 is used in conjunction with a sauna. One of skill in the art will appreciate, however, that method 1200 and the other systems and methods in accordance with the present invention may be utilized in a variety of scenarios and for a variety of purposes other than a sauna application.

Figure 13:
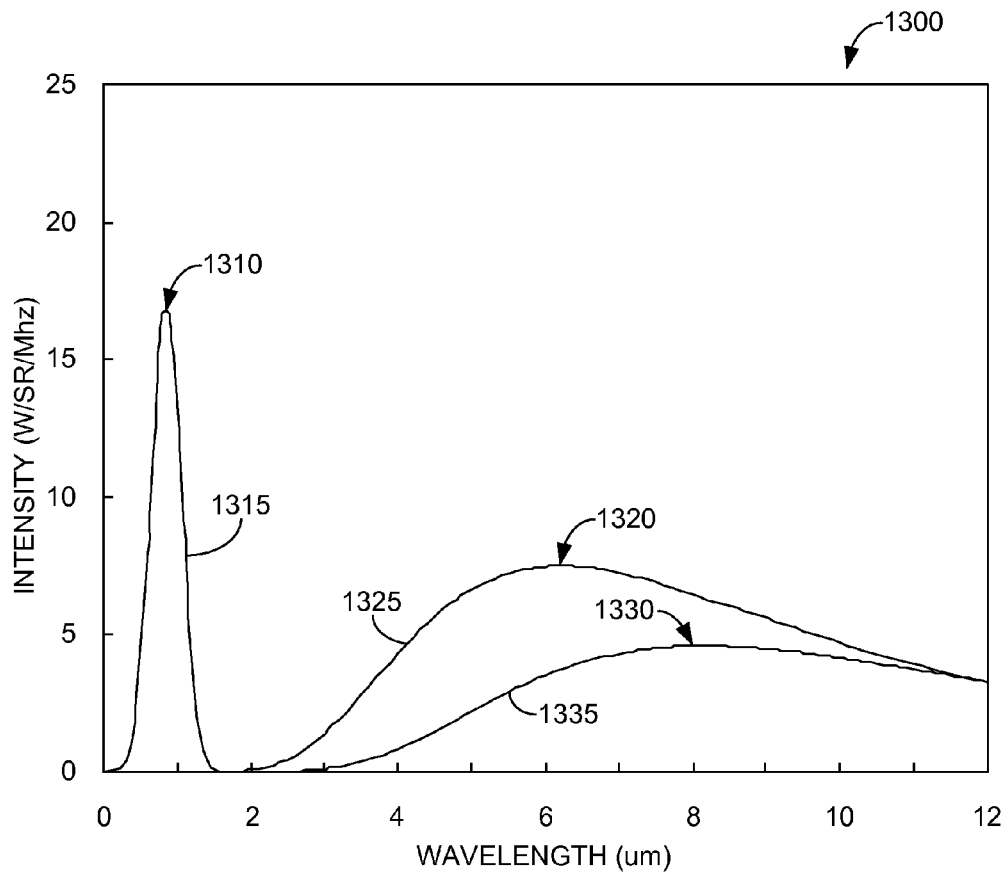
FIG. 13 illustrates an example of multi-peak infrared spectrum that may be obtained using systems and methods in accordance with the present invention.

Referring now to FIG. 13, an example of an infrared spectrum 1300 with multiple peak wavelengths, such as may be obtained using systems and methods in accordance with the present invention, is illustrated. A near-infrared peak 1310 of a near-infrared spectrum 1315 may be emitted by one or more near-infrared emitters. A mid-infrared peak 1320 of a mid-infrared spectrum 1325 may be emitted by one or more mid-infrared emitters. A far-infrared peak 1330 of a far-infrared spectrum 1335 may be emitted by one or more far-infrared emitters. An individual emitter may be permanently dedicated or tuneable to emitting in the near-infrared, mid-infrared, and/or far-infrared. One of skill in the art will appreciate that an emitter may have a peak wavelength in one portion of the infrared spectrum but still emit at lower powers in other wavelengths. The precise shape of a spectrum will depend upon the material and power of an emitter. Generally, near-infrared ranges from about 0.75-1.5 mm, mid-infrared ranges from about 1.5-7 mm, and far-infrared ranges from about 7 mm and higher. The power of a given peak may be varied, for example, by increasing or decreasing the number of emitters operating at that peak wavelength.

Embodiments of the present invention provide for a sauna integrated within a smart home environment such that various settings associated with the sauna can be controlled from various locations in the home, or even from locations remote from the home. Other embodiments provide for a sauna that is integrated within a network of saunas or other devices. Still further embodiments provide for a sauna having any combination or all of the various features described herein.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well-adapted to attain all the ends and objects set forth above, together with other advantages which are obvious and inherent to the system and method. It will be understood that certain features and subcombinations are of utility and may be employed without reference to other features and subcombinations. This is contemplated by and is within the scope of the claims.

What is claimed is:

1. A sauna comprising:
an enclosure assembly for accommodating a user;
at least one infrared emitter coupled with the enclosure assembly and operable to emit infrared radiation over at least two different specified wavelength-ranges in the infrared-wavelength spectrum, wherein each specified wavelength-range comprises one of near-infrared radiation, mid-infrared radiation, and far-infrared radiation;
wherein the at least one infrared emitter comprises at least one heating element selected from, at least one array of LEDs, an element containing ceramic particles with a nanometer scale dimension, a carbon-containing planar heating element and a heating element on a polyimide film substrate; and
at least one driver module coupled to the at least one infrared emitter and operable to control the at least one infrared emitter to emit infrared radiation over one of the at least two specified wavelength-ranges in the infrared wavelength spectrum, wherein a heat control module operably coupled to the at least one driver module and operable to allow a user to fixedly specify desired output infrared radiation over the wavelength-range associated with each of the at least one infrared emitter.

2. The sauna of claim 1, wherein each infrared emitter comprises any of one or more near-infrared radiation emitting elements, one or more mid-infrared radiation emitting elements, and one or more far-infrared radiation emitting elements.

3. The sauna of claim 2, wherein the at least one driver module is further operable to control infrared radiated power output of at least one infrared emitter using pulse width modulation.

4. The sauna of claim 1, wherein the at least one infrared emitter comprises a plurality of infrared heating elements; and a plurality of thermocouples operable to independently control each of the plurality of infrared heating elements.

5. The sauna of claim 4, wherein the at least one infrared emitter comprises a first and second infrared emitter operable independently of one another at two specified wavelength-ranges.

6. The sauna of claim 5, wherein the first and second infrared emitters simultaneously emit infrared radiation within a plurality of zones corresponding to a body region of the user.

7. The sauna of claim 1, wherein the at least one infrared emitter comprises at least two infrared heating elements emitters, each of the at least two infrared emitters operable to emit infrared heat at different specified wavelength-ranges.

8. A sauna comprising:
an enclosure assembly for accommodating a user;
a first infrared emitter coupled with the enclosure assembly, the first infrared emitter comprising a first infrared heating element operable at a first wavelength-range and a second infrared heating element, different from the first heating element, operable at a second wavelength-range different than the first wavelength range, and wherein the first wavelength-range and the second wavelength-range each comprise one of near-infrared radiation, mid-infrared radiation, and far-infrared radiation;
wherein the first infrared emitter and the second infrared emitter comprise at least one heating element selected from, at least onne array of LEDs, an element containing ceramic particles with a nanometer scale dimension, a carbon-containing planar heating element and a heating element on a polyimide film substrate; and
a first driver module operable to control the first heating element and a second driver module operable to control the second heating element such that the first and second infrared emitters are controlled independently of one another.

9. The sauna of claim 8, further comprising a second infrared emitter coupled with the enclosure comprising at least one infrared heating element, the second infrared emitter operable at a specified wavelength-range, wherein the specified wavelength-range comprises one of near-infrared radiation, mid-infrared radiation, and far-infrared radiation; and
a third driver module operable to control the second infrared emitter independently of the first heating element and the second heating element.

10. The sauna of claim 8, wherein the first heating element, the second heating element and the second infrared emitter are operable to each simultaneously emit adjustable infrared radiation, wherein the first heating element emits infrared radiation at a first body region of the user; the second heating element emits infrared radiation at a second body region of the user, and the second infrared emitter emits infrared radiation at a third body region of the user.

11. The sauna of claim 8, wherein each of the first infrared emitter and the second infrared emitter comprises any of one or more near-infrared radiation emitting elements, one or more mid-infrared radiation emitting elements, and one or more far-infrared radiation emitting elements.

12. A sauna comprising:
an enclosure assembly for accommodating a user;
at least one infrared emitter coupled with the enclosure assembly and operable to emit infrared radiation over at least two different specified wavelength-ranges in the infrared-wavelength spectrum, wherein each specified wavelength-range comprises one of near-infrared radiation, mid-infrared radiation, and far-infrared radiation;
the at least one infrared emitter comprising at least one heating element selected from a carbon-containing planar heating element operable to emit far-infrared radiation and a heating element on a polyimide film substrate, at least one array of first LED heating elements operable to emit mid-infrared radiation and at least one array of second LED heating elements operable to emit near-infrared radiation; and at least one driver module coupled to each of the at least one planar heating element, the at least one array of first LED heating elements and the at least one array of second LED heating elements and operable to control the at least one planar heating element to emit far-infrared radiation, the at least one array of second LED heating elements to emit mid-infrared radiation and the at least one array LED heating elements to emit near-infrared radiation.

\* \* \* \* \*